(12) United States Patent
Dedick et al.

(10) Patent No.: US 11,964,235 B1
(45) Date of Patent: Apr. 23, 2024

(54) APPLICATION OF STRUCTURALLY ALTERED GAS MOLECULES TO ENHANCE WATER TREATMENT AND DESALINATION PROCESSES

(71) Applicants: H2Plus LLC, San Diego, CA (US); H2Plus Operations, LLC, San Diego, CA (US)

(72) Inventors: Gene Dedick, Grand Junction, CO (US); Jared Roberts, Grand Junction, CO (US)

(73) Assignees: H2Plus LLC, San Diego, CA (US); H2Plus Operations, LLC, San Diego, CA (US)

( * ) Notice: Subject to any disclaimer, the term of this patent is extended or adjusted under 35 U.S.C. 154(b) by 0 days.

(21) Appl. No.: 18/376,741

(22) Filed: Oct. 4, 2023

Related U.S. Application Data

(63) Continuation-in-part of application No. PCT/US2022/044167, filed on Sep. 21, 2022, which is a continuation of application No. 17/487,613, filed on Sep. 28, 2021, now Pat. No. 11,384,440, application No. 18/376,741, filed on Oct. 4, 2023 is a continuation-in-part of application No. PCT/US2022/044168, filed on Sep. 21, 2022, which
(Continued)

(51) Int. Cl.
| | | |
|---|---|---|
| *B01D 61/04* | (2006.01) | |
| *B01D 61/02* | (2006.01) | |
| *C01B 5/00* | (2006.01) | |
| *C02F 1/44* | (2023.01) | |
| *C02F 1/469* | (2023.01) | |
| *C02F 1/48* | (2023.01) | |
| *C02F 1/66* | (2023.01) | |
| *B03C 9/00* | (2006.01) | |
| *C02F 103/08* | (2006.01) | |
| *C25B 1/044* | (2021.01) | |

(52) U.S. Cl.
CPC .......... *B01D 61/04* (2013.01); *B01D 61/025* (2013.01); *C01B 5/00* (2013.01); *C02F 1/441* (2013.01); *C02F 1/469* (2013.01); *C02F 1/481* (2013.01); *C02F 1/66* (2013.01); *B01D 2311/04* (2013.01); *B01D 2311/2603* (2013.01); *B01D 2311/2607* (2013.01); *B01D 2311/2661* (2013.01); *B03C 9/00* (2013.01); *C02F 2103/08* (2013.01); *C02F 2201/48* (2013.01); *C02F 2209/04* (2013.01); *C25B 1/044* (2021.01)

(58) Field of Classification Search
None
See application file for complete search history.

(56) References Cited

U.S. PATENT DOCUMENTS 11,384,440 B1 * 7/2022 Roberts .................... C25B 1/04
11,634,823 B2    4/2023 Roberts et al.
(Continued)

*Primary Examiner* — Clare M Perrin
(74) *Attorney, Agent, or Firm* — Georgiy L. Khayet

(57) ABSTRACT

Methods and systems for enhancing water treatment and desalination are provided. An example method includes generating structurally altered gas molecules from water, where the structurally altered gas molecules have a higher probability of attraction of electrons into areas adjunct to the structurally altered gas molecules than molecules of the water. The method further includes mixing the structurally altered gas molecules with raw water to modify properties of the raw water, thereby increasing raw water filtering efficiency of a water filtering system.

20 Claims, 13 Drawing Sheets

Related U.S. Application Data is a continuation of application No. 17/743,632, filed on May 13, 2022, now Pat. No. 11,634,823, which is a continuation of application No. 17/487,613, filed on Sep. 28, 2021, now Pat. No. 11,384,440, said application No. PCT/US2022/044168 is a continuation of application No. 17/487,613, filed on Sep. 28, 2021, now Pat. No. 11,384,440.

(56) References Cited

U.S. PATENT DOCUMENTS

2017/0368528 A1* 12/2017 Gourley .................... C25B 9/05
2020/0308037 A1* 10/2020 Alamoudi ............ B01D 61/026

* cited by examiner

| NO TREATMENT | | | | | | | |
|---|---|---|---|---|---|---|---|
| Date | Time | TDS Feed | TDS Product | TDS RO Reject | ORP RO Product | pH RO Product | Temp RO Product |
| | | ppm | ppm | ppm | mV | pH | deg F |
| day one | 12:03 PM | 11,000 | 336 | 11,850 | 69 | 8.11 | 64.1 |
| day one | 12:45 PM | 11,000 | 328 | 11,850 | 61 | 8.17 | 63.7 |
| day one | 1:00 PM | 11,000 | 320 | 11,850 | 64 | 8.10 | 63.7 |
| day one | 1:15 PM | 11,000 | 306 | 11,850 | 65 | 8.19 | 63.9 |
| AVG | | 11,000 | 323 | 11,850 | 65 | 8.14 | 63.9 |
| | | | Salt Rejection % | | 97.1% | | |

| WITH TREATMENT | | | | | | | |
|---|---|---|---|---|---|---|---|
| Date | Time | TDS Feed | TDS Product | TDS RO Reject | ORP RO Product | pH RO Product | Temp RO Product |
| | | ppm | ppm | ppm | mV | pH | deg F |
| day one | 2:15 PM | 11,000 | 282 | 11,850 | -45 | 8.37 | 64.4 |
| day one | 2:30 PM | 11,000 | 274 | 11,850 | -46 | 8.37 | 64.6 |
| day one | 2:45 PM | 11,000 | 265 | 11,850 | -48 | 8.38 | 64.4 |
| day one | 3:00 PM | 11,000 | 254 | 11,850 | -49 | 8.39 | 64.8 |
| AVG | | 11,000 | 269 | 11,850 | -47 | 8.38 | 64.6 |
| | | | Salt Rejection % | | 97.6% | | |

| WITH TREATMENT | |
|---|---|
| % Increase in Salt Rejection | 17.2% |
| % Decrease in TDS, (ppm) | 16.7% |

NO TREATMENT

| RO Transmembrane Pressure | RO Feed Flow | RO Product Flow | RO Reject Flow | Minimum Osmotic Pressure to generate flow |
|---|---|---|---|---|
| PSIG | GPM | GPM | GPM | psig |
| 199 | 1.247 | 0.117 | 1.13 | 94 |
| 199 | 1.247 | 0.117 | 1.13 | |
| 199 | 1.247 | 0.117 | 1.13 | |
| 199 | 1.247 | 0.117 | 1.13 | |
| 199 | 1.25 | 0.12 | 1.13 | |

WITH TREATMENT

| RO Transmembrane Pressure | RO Feed Flow | RO Product Flow | RO Reject Flow | Minimum Osmotic Pressure to generate flow |
|---|---|---|---|---|
| PSIG | GPM | GPM | GPM | psig |
| 199 | 1.247 | 0.286 | 0.961 | 72 |
| 199 | 1.247 | 0.286 | 0.961 | |
| 199 | 1.247 | 0.286 | 0.961 | |
| 199 | 1.247 | 0.286 | 0.961 | |
| AVG 199 | 1.25 | 0.286 | 0.961 | |
| | | % Increase in RO Prod Flow | % Decrease in RO Rej Flow | |
| | | 13.6% | 13.6% | |

FIG. 4

| USING | TREATMENT | | |
|---|---|---|---|
| Decrease in Osmotic Pressure to Generate Flow | | | 23.4% |
| 23.4% Savings on 16.47 kWh/Kgal - (Assume $.10 USD per kWh) | | | $0.39 |
| Avg Energy Consumption of Medium and Large Scale RO Plants Worldwide | | 4.35 kWh / M3, (16.47 kWh / Kgal) | |
| MEDIUM RO PLANT ECONOMIC & SUSTAINABILITY BENEFITS SUMMARY | | | |
| Avg Medium RO Plant Daily Flow | 30,000 M3 (7,925 KGals) | | |
| 13.6% increase annual water production (Kgals) | | | 676,997 |
| Annual Freshwater Production increase, ($USD) at $4.00 per Kgal | | | $2,707,989 |
| 13.6% Annual Decrease in Waste Water Produced at 50% RO Recovery (Kgals) | | | 196,012 |
| Annual Wastewater Savings ($USD) at $6.00 per Kgal | | | $1,176,071 |
| Annual Electrical Savings ($USD) Medium RO Plant ($.10 per kWh) | | | $1,115,015 |
| Total Annual Water, Waste Water & Energy Savings | | | $4,999,075 |
| MEDIUM RO PLANT SUSTAINABILITY BENEFITS SUMMARY | | | |
| Annual Decrease in Wastewater Volume Released to Enviornment (Gallons) | | | 196,011,879 |
| Annual Metric Tons CO2 kept from Atmosphere with Energy Savings | | | 10,081 |
| Carbon footprints neutralized (14 MT per person per yr Avg) | | | 720 |
| LARGE RO PLANT ECONOMIC BENEFITS SUMMARY | | | |
| Avg Large RO Plant Daily Flow | 120,000 M3 (31,701 KGals) | | |
| 13.6% increase annual water production (Kgals) | | | 1,569,144 |
| Annual Freshwater Production increase, ($USD) at $4.00 per Kgal | | | $6,272,578 |
| 13.6% Annual Decrease in Waste Water Produced at 50% RO Recovery (Kgals) | | | 784,072 |
| Annual Wastewater Savings ($USD) at $6.00 per Kgal | | | $4,704,433 |
| Annual Electrical Savings ($USD) ($.10 per kWh) | | | $4,460,199 |
| Total Annual Water, Waste Water & Energy Savings | | | $15,437,211 |
| LARGE RO PLANT SUSTAINABILITY BENEFITS SUMMARY | | | |
| Annual Decrease in Wastewater Volume Released to Enviornment (Gallons) | | | 784,072,247 |
| Annual Metric Tons CO2 kept from Atmosphere with Energy Savings | | | 40,326 |
| Carbon footprints neutralized (14 MT per person per yr Avg) | | | 2,880 |

FIG. 5

| Parameter | Control | Restructured | p-value |
|---|---|---|---|
| System electrical power (watts) | 944.2 ± 37.7 | 947.4 ± 42.0 | 0.16 |
| System flow (gallons/min) | 1.59 ± 0.06 | 1.61 ± 0.05 | 0.24 |
| System volume (gallons) | 191.80 ± 17.99 | 197.74 ± 4.57 | 0.26 |
| Waste flow (gallons/min) | 1.16 ± 0.05 | 1.19 ± 0.09 | 0.23 |
| Waste volume (gallons) | 145.14 ± 8.50 | 147.82 ± 8.47 | 0.35 |
| Waste TDS (mg/l) | 10866.7 ± 1591.7 | 12358.3 ± 1574.3 | 0.10 |
| Product flow (kg/min) | 1.027 ± 0.127 | 1.025 ± 0.139 | 0.49 |
| Product volume (gallons) | 32.703 ± 3.943 | 32.688 ± 4.534 | 0.50 |
| Product TDS (inline) (mg/l) | 432.8 ± 107.9 | 324.3 ± 110.8 | 0.04 |
| Product TDS (meter) (mg/l) | 441.3 ± 84.5 | 341.1 ± 75.0 | 0.02 |
| Product ORP (mV) | 195.8 ± 29.6 | -192.5 ± 13.3 | <0.001 |
| Product pH | 6.036 ± 0.131 | 6.803 ± 0.320 | <0.001 |

APPLICATION OF STRUCTURALLY ALTERED GAS MOLECULES TO ENHANCE WATER TREATMENT AND DESALINATION PROCESSES

TECHNICAL FIELD

This disclosure relates to methods for deploying a structurally altered gas molecule to enhance water treatment and desalination processes.

BACKGROUND

Because of the rapid growth of the world population and rising water needs in the industrial and domestic spaces, there are water shortage problems. Last century, as the global population quadrupled, the world water demand have increased sevenfold. Approximately 0.5% of the water that currently exists on Earth is drinkable without extensive pretreatment. At present that equates to 2.2 million gallons per person. Current usage estimates of 1,004 gallons per person per day conclude that each person on our planet has about 6 years of water reserves for personal, agricultural, commercial, and industrial consumption on per capita basis. This estimate assumes no increase in population. Knowing that the average lifespan is about 12 times the 6-year water reserve, the current and future demands for water will continue to be met by treating non-potable water with the best available technologies. Excluding the 2% of the Earth's fresh water supply locked up in glaciers, 97%+ of the remaining water resides in the Earth's oceans.

The problem of water scarcity is not only a problem of appropriate techniques to treat the water, but also a social and educational problem relying on national and global endeavors as well as on technical solutions. To address water shortage problems, strategies that include recycling/repurposing water, and minimization of water use have been developed. Many techniques have been developed including gravity precipitation, ion exchange, selective ion separation, distillation, reverse osmosis (RO) membrane separation, mechanical vapor pressure compression, electrodialysis and nanofiltration processes. Membrane separation processes are gaining global acceptance in both water treatment and desalination due to their simplicity and relatively low cost compared to other treatment technologies. RO membranes can be effectively used to remove salts and other pollutants from brackish water. The water is transferred through the RO membrane by diffusion, while the salt is rejected by size exclusion and repulsion electrostatic force between the membrane surface and dissolved ions, which is caused by charge difference. For efficient separation, the membranes must be permeable to water, impermeable to solutes, and capable of tolerating high operating pressures.

SUMMARY

This summary is provided to introduce a selection of concepts in a simplified form that are further described in the Detailed Description below. This summary is not intended to identify key features or essential features of the claimed subject matter, nor is it intended to be used as an aid in determining the scope of the claimed subject matter.

According to one example embodiment of the present disclosure, a method for enhancing water treatment and desalination is provided. The method may include generating structurally altered gas molecules from water, where the structurally altered gas molecules have a higher probability of attraction of electrons into areas adjunct to the structurally altered gas molecules than molecules of the water. The method may further include admixing the structurally altered gas molecules to raw water to modify properties of the raw water, thereby increasing raw water filtering efficiency of a water filtering system.

According to another embodiment of the present disclosure, a system for enhancing water treatment and desalination is provided. The system may include a chemical reaction chamber configured to accommodate water. The system may further include a magnetic field generator configured to generate a focused magnetic field. The system may further include an electric field generator configured to generate an electric field. The electric field and the focused magnetic field drive a chemical reaction in the chemical reaction chamber to generate structurally altered gas molecules from the water. The structurally altered gas molecules have a higher probability of attraction of electrons into areas adjunct to the structurally altered gas molecules than molecules of the water. The system may further include a mixing chamber configured to admix the structurally altered gas molecules to raw water to modify properties of the raw water, thereby increasing raw water filtering efficiency of a water filtering system.

Other example embodiments of the disclosure and aspects will become apparent from the following description taken in conjunction with the following drawings.

BRIEF DESCRIPTION OF DRAWINGS

Exemplary embodiments are illustrated by way of example and not limitation in the figures of the accompanying drawings, in which like references indicate similar elements.

FIG. 3 shows a table illustrating water analysis before and after treatment according to the present disclosure.

FIG. 4 shows a table illustrating transmembrane and osmotic pressure and flow data before and after treatment according to the present disclosure.

FIG. 5 shows a table illustrating economic and sustainability data on brackish/seawater RO membranes according to the present disclosure.

DETAILED DESCRIPTION

Figure 1:
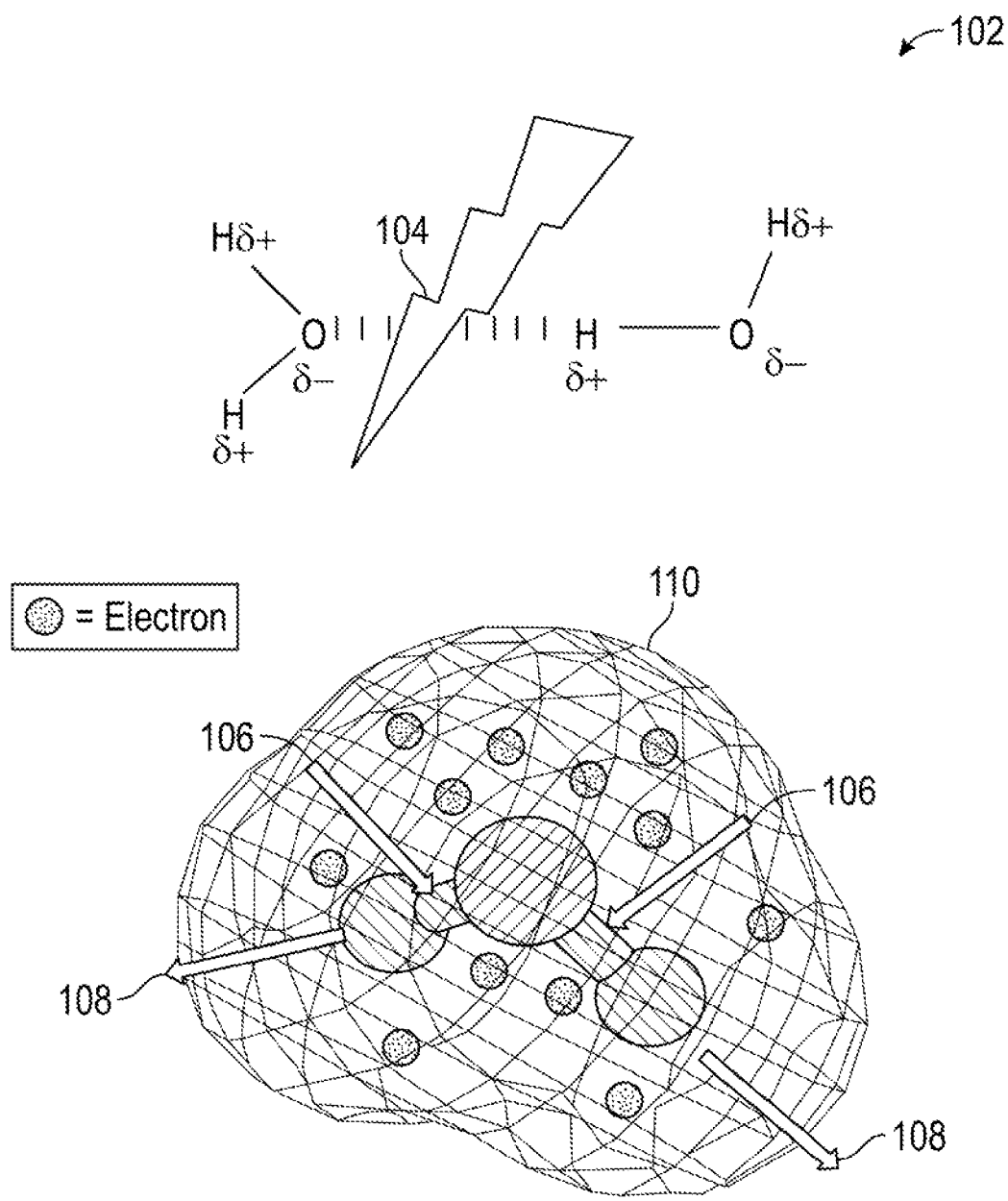
FIG. 1 shows a structurally altered gas molecule according to the method of the present disclosure.

The following detailed description of embodiments includes references to the accompanying drawings, which form a part of the detailed description. Approaches described in this section are not prior art to the claims and are not admitted to be prior art by inclusion in this section. The drawings show illustrations in accordance with example embodiments. These example embodiments, which are also referred to herein as "examples," are described in enough detail to enable those skilled in the art to practice the present subject matter. The embodiments can be combined, other embodiments can be utilized, or structural, logical, and operational changes can be made without departing from the scope of what is claimed. The following detailed description is, therefore, not to be taken in a limiting sense, and the scope is defined by the appended claims and their equivalents.

Generally, the embodiments of this disclosure relate to methods for deploying a structurally altered gas molecule to create a stable alternative molecular structure of water ($H_2O$). The methods of the present disclosure enhance water treatment and desalination processes and increase the effectiveness of process fluid and water treatment technologies.

The method of the present disclosure uses conventional water treatment technologies to generate a purified liquid. The purified liquid is added to a chemical reaction chamber containing an electrolyte solution. This mixture is treated by a focused magnetic field using a magnetic field generator and an electric field to generate an altered, gaseous form of the purified liquid. The generated altered water molecule gas can then be deployed directly or mixed into the liquids that interface with process fluid and water treatment processes to increase the efficiency of their subcomponents. The process fluid and water treatment processes may include but not limited to gravity precipitation, ion exchange, selective ion separation, distillation, RO membrane separation, mechanical vapor pressure compression, electrodialysis, and nanofiltration processes.

Components involved in a method described in the present disclosure include water, water pretreatment equipment, reaction chamber, electrolyte solution, a magnetic field generator, and electricity. Additional components may include pressure regulators, an electrical inverter, solar panels, and a gas diffuser for diffusing gas into atmosphere or liquid that living cells can interface with and uptake the altered water molecule in gaseous and/or liquid form.

Water serves as the raw material that the gas product is generated from. Water pretreatment equipment is used to prepare the water for the reaction chamber using such steps as conventional filtration, absorption, and purification. The reaction chamber provides the reaction vessel that holds the electrolyte solution and the purified water for the magnetic field to chemically convert the purified water into an altered gaseous form of the purified liquid. The electrolyte solution provides the medium for the magnetic field to align and impart its energy on the purified water mixed in with the electrolyte solution to chemically generate the altered gaseous form of the water. In an example embodiment, the magnetic field generator may include one of the following: earth magnets, solenoids, electromagnets, and so forth. The magnetic field generator, creates magnetic field to drive the chemical reaction that generates the altered form of the gaseous water. Once generated, the gas can be diffused into the upstream and or recycled liquid feed stream.

In some embodiments, a high efficiency gas may be added to a liquid deployment system to optimize the desired physical diffusion and resulting chemical kinetics/thermodynamic benefits.

Conventional energy intensive mixing processes typically provide mediocre results. The method of the present disclosure provides enhanced contaminant removal and resulting benefits as described below.

Referring now to the drawings, various embodiments are described in which like reference numerals represent like parts and assemblies throughout the several views. It should be noted that the reference to various embodiments does not limit the scope of the claims attached hereto. Additionally, any examples outlined in this specification are not intended to be limiting and merely set forth some of the many possible embodiments for the appended claims.

This application makes reference to U.S. patent application Ser. No. 17/487,613, filed on Sep. 28, 2021, now U.S. Pat. No. 11,384,440, and to U.S. patent application Ser. No. 17/743,632, filed on May 13, 2022, now U.S. Pat. No. 11,634,823, the subject matter of which is incorporated herein by reference in its entirety for all purposes. Processes and systems described herein may be better understood in light of the concepts found in these references.

FIG. 1 shows a structurally altered gas molecule 102 deployed in the method of the present disclosure. The structurally altered gas molecule deployed in the method of the present disclosure may include a structurally altered gas molecule generated by processes described in U.S. Pat. Nos. 11,384,440 and 11,634,823.

During the alterations, hydrogen bonds 104 are broken to allow a gaseous single molecule form of water to exist and enable the following adjustments: 1) a bond angle 106 is decreased; 2) oxygen-hydrogen covalent bond length 108 is increased; 3) adjustments allow room for more electrons in probability spheres 110. Per the molecular orbital theory (MOT), small molecules like water can adjust electron energy levels around the probability spheres. The MOT states that not just the atoms themselves but the entire molecule shares electrons now.

As for the structurally altered gas molecule 102, the molecular alterations include lengthening of the H—O bonds from 0.95 Angstroms up to 1.3 Angstrom and decreasing the H—O—H bond angle from 104.5° to as small as 94°. These changes alter the chemical properties of the water that the gas may be infused into. These changes include a decrease in normal pure water pH (from 7.0 to ~6.5), and a shift in redox potential from 0 mV to ~−200 mV. This gas has been diffused into normal pure water where it has been demonstrated that the infused gas imparts some of its above-described properties to the un-gassed normal pure water.

The restructuring of liquid un-gassed diffused normal water molecules by diffusion of the structurally altered gas molecules 102 into the normal un-gassed diffused liquid water has provided a number of observed alterations in the gas diffused water. The first alteration is reduction in intermolecular hydrogen bonding between water molecules in liquid phase. Hydrogen bonding in water is a dynamic attraction between positively charged hydrogen atoms of one water molecule and negatively charged oxygen atoms of another water molecule. This occurs because of the difference in electronegativity between hydrogen and oxygen atoms.

The second alteration is reduction in the dipole moment of the gas treated water. The dipole moment is a measure of the separation of positive and negative electrical charges within a system. Water has a dipole moment because water has a bent structure and the electronegativity difference between atoms of oxygen and hydrogen.

The third alteration is reduction in the ion-dipole force formed between ions and water. The ion-dipole force is a force of attraction between an ion and a neutral molecule that has a dipole.

These alterations reduce the tendency of the water molecules to "clump" through hydrogen bonding, and its dipole moment. The alterations also provide a reduction in the ion-dipole force formed between ions and water to facilitate the separation and passage of individual water molecules through ion water separation technologies used in the separation of ions, (both soluble and insoluble), from process fluids and in the purification of water. With these changes provided by the structurally altering gas molecules, the desirable effects on the chemical kinetics (speed of reaction) and thermodynamics (how far to completion the reactions may go) have been demonstrated.

Passage of individual water molecules through water treatment processes, separation technologies and membranes used for purification of water by altering the ion-ion, ion-water and water-water interactions in solution have been demonstrated and documented two experiments conducted using the method of the present disclosure and described below in the present disclosure. Results from the first experiment conclude a significant reduction in water and energy consumption, and increased sustainability benefit when using the method of the present disclosure in brackish/seawater RO desalinization applications. In the second experiment, efficiency improvements of 25% in salt removal efficiency have been documented all other consumables being equal.

The gas, i.e., structurally altered gas molecules, can be deployed directly to public and private influent water, industrial process water and wastewater streams to enhance the performance of the existing technology and, in some cases, eliminate the need for existing sub-components and their corresponding capital and operational costs.

The method of the present disclosure was studied in two experiments conducted using the method of the present disclosure. In all experiments, the only variable introduced was the testing with and without the presence of the structurally altered gas molecule. In the first experiment, the same test membrane was used in before and after no-gas then gassed brackish water experiment. In the second experiment, a new test membrane was used for each test.

The first experiment is the desalination experiment using the method of the present disclosure as a reverse osmosis membrane pretreatment.

Purpose of the experiment. The purpose of the first experiment is to compare the effects of the method of the present disclosure on improving the efficiency of thin film composite RO membranes on brackish/seawater applications with and without the pretreatment by the method of the present disclosure. The key metrics used for this experiment are the measurement of RO membrane salt rejection, RO membrane product water total dissolved solids (TDS) reduction, RO membrane percent product recovery, RO membrane percent reject volume and the change in osmotic pressure required to initiate flow through the same RO membrane without and with the pretreatment by the method of the present disclosure. Improvement of these metrics may confirm increased product water quality, increased product water volume, and decreased wastewater volume, all at a significant reduction in energy consumption with increased sustainability benefit.

Materials & Methods. 30.024 lbs. of powdered instant seawater sea salt were dissolved in 2,502 lbs. (300 US Gallons) of 64.6 degrees Fahrenheit RO water. The RO water was measured at 3 ppm TDS or less when it was used to dissolve the salt. These contents were mixed in a 330-gallon polyethylene food grade tote with a simple stainless steel propeller mixer until all of the sea salt was completely dissolved. The manufactured brackish/seawater mixture was then pumped through a single pass 4×40SSMH thin film composite RO membrane with no pretreatment or prefiltration.

A Grundfos SCALA 2 Constant Pressure Pump was used for pumping the salt solution through the RO membrane. The RO transmembrane pressure was held at 199 pounds per square inch gauge (psig) for the entirety of its operation during this experiment.

Product water TDS, Oxidation Reduction Potential (ORP), pH, temperature, pressure and flow measurements were made real time during this experiment. Measuring devices used were the following: a Milwaukee PRO EC/TDS/Temp Probe, an APERA ORP60 Tester, a HANNA HI98129 pH/Conductivity/TDS Tester, an oil filled WIKA Type 0-300 psig FLW Instrument pressure gauge, and Pyrex 2,000 ml graduated volumetric flasks. RO Feedwater, Product Water & Reject water were measured. Samples of these streams were subjected to laboratory analysis.

Two 1-hour long runs were made in this experiment where the manufactured brackish/seawater was pumped through the RO membrane. The aforementioned tests and samples were taken at 15-minute intervals. The first 1-hour long run was performed without the infusion of the gas including structurally altered gas molecules. The second 1-hour long run was made with the infusion of the gas including structurally altered gas molecules. The gas was fed at a constant rate. Transmembrane pressure was held at 199 psig in during all runs.

Figure 2:
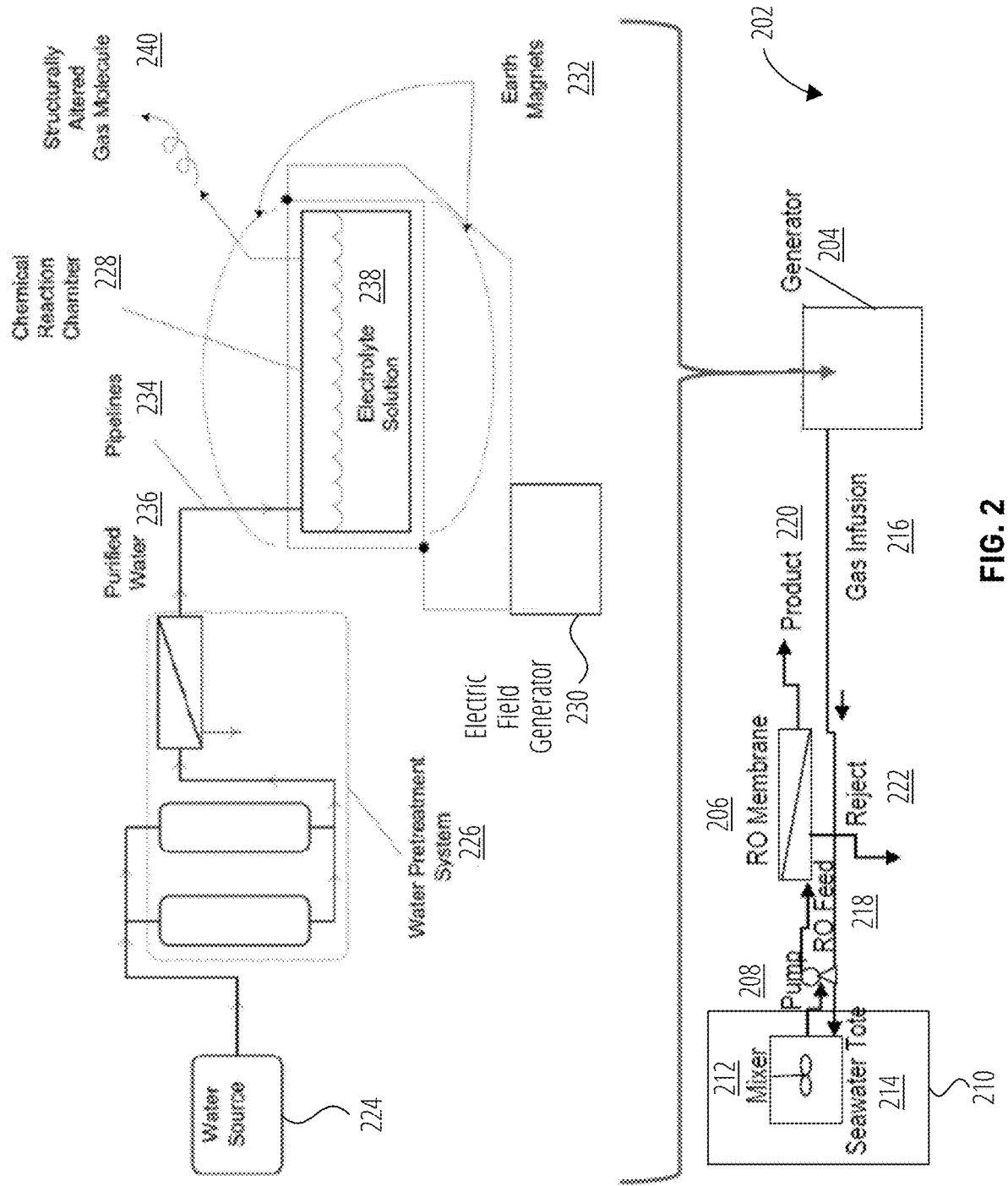
FIG. 2 is a diagram showing an RO membrane test system used in an experiment.

FIG. 2 is a diagram showing a system 202 for enhancing water treatment and desalination, according to an example embodiment. The system 202 may have a technology generator shown as a generator 204, a RO membrane 206, a pump 208, and a mixing chamber 210 that is a combination of a mixer 212 and a reservoir shown as a seawater tote 214.

The water infused with structurally altered gas molecules generated by the generator 204 is provided in the form of gas infusion 216 to the seawater tote 214 of the mixing chamber 210. The seawater tote 214 may be filled with raw water, such as sea water. The mixer 212 of the mixing chamber 210 may be installed in the seawater tote 214 for mixing the water infused with structurally altered gas molecules with the raw water to modify properties of the raw water, thereby increasing raw water filtering efficiency of a water filtering system shown as the RO membrane 206.

Upon admixing the structurally altered gas molecules and the raw water to modify properties of the raw water, the raw water with modified properties is provided to the pump 208. The pump 208 provides the raw water with modified properties in form of the RO feed 218 to the RO membrane 206. The RO membrane 206 filters the raw water with modified properties and produces a product 220 and a reject 222 (i.e., substances and particles filtered by the RO membrane 206). The product 220 is water having modified properties and filtered by the RO membrane 206.

The generator 204 is an example system for generating a structurally altered gas molecule, according to an example embodiment. The generator 204 may include a water source 224, a water pretreatment system 226, a chemical reaction chamber 228, an electric field generator 230, a magnetic field generator, e.g., earth magnets 232, and pipelines 234. The generator 204 may also include pressure regulators. The electric field generator 230 may include an electrical inverter and solar panels.

The water source 224 may provide water as a raw material for generating the gas molecule product. The water pretreatment system 226 may prepare the water for the chemical reaction chamber 228. The water pretreatment system 226 may include a filtration system, an absorption system, and a purification system to produce the purified water 236.

The chemical reaction chamber 228 may be configured to accommodate water and may contain an electrolyte solution 238. The electrolyte solution 238 can be made using a mixture of a hydroxide salt and an acid salt. The purified water 236 can be provided to the chemical reaction chamber 228. The earth magnets 232 may generate a permanent focused magnetic field. The electric field generator 230 may generate an electric field. The focused magnetic field and the electrical field may drive a chemical reaction that generates the structurally altered gas molecule 240 from the purified water supplied into the chemical reaction chamber 228. The electrolyte solution 238 may provide a medium for the focused magnetic field to align and impart energy of the focused magnetic field on the purified water mixed in with the electrolyte solution and, thereby, chemically generate the structurally altered gas molecule 240 from the purified water 236. The temperature in the chemical reaction chamber 228 can be from 60 degrees to 120 degrees Fahrenheit. The pressure in the chemical reaction chamber 228 can be from 1 atmosphere to 40 psig. The structurally altered gas molecule 240 may have a higher probability of attraction of electrons into areas adjunct to the structurally altered gas molecule 240 than molecules of the water.

The structurally altered gas molecule 240 can be 99.9% hydrogen and oxygen combination in two parts of hydrogen to one part of oxygen ratio at the standard temperature of 68 degrees Fahrenheit and pressure of 1 atmosphere (STP). The structurally altered gas molecule 240 may have the O—H bond length between 0.95 and 1.3 angstroms and the H—O—H bond angle between 94 degrees and 104 degrees.

The molecular weight of the structurally altered gas molecule 240 can be between 12.14 and 12.18 atomic mass units (AMUs) at STP. In comparison, the molecular weight of pure water vapor is 18 AMUs at STP. At STP, the relative density of the structurally altered gas molecule 240 compared to dry air is 41.18%-42.00%. In comparison, relative density of pure water vapor compared to dry air is 62.19%. The structurally altered gas molecule 240 may remain stable at pressure more than 300 psig.

When dissolved in pure water having 2 parts per million (ppm) of TDS at 25 degrees Celsius, the structurally altered gas molecule 240 may generate an ORP of approximately −50 to −360 mV and a pH of 6.1 to 6.8 in the resulting gas-water mixture. The ORP and pH may remain stable in a closed insoluble vessel for at least 30 days. In comparison, the pure water does not possess a stable negative ORP at a pH below 7.

When dissolved in pure water (2 ppm TDS at 25 degrees Celsius), the structurally altered gas molecule 240 may reduce the concentration of TDS from 2.0 ppm to 1.0 ppm, i.e., the reduction is 50%. Barring contamination, the concentration of TDS remains stable at 1 ppm in a closed insoluble vessel indefinitely.

The changes in structure and properties of the structurally altered gas molecule 240 are caused by changes in electronic structure of the gas structurally altered structurally altered gas molecule 240 due to applying the focused magnetic field and the electrical field to the mixture of the electrolyte solution 238 and purified water 236.

In an example embodiment, a structurally altered gas molecule 240 used in the method for enhancing water treatment and desalination is a combination of two parts of hydrogen and one part of oxygen and produced from water. The structurally altered gas molecule 240 is produced by placing an electrolyte solution in a chemical reaction chamber, adding purified water to the chemical reaction chamber, and applying a focused magnetic field generated by a magnetic field generator and an electric field to a mixture of the purified water and the electrolyte solution to cause generation of the structurally altered gas molecule from the purified water. The temperature in the chemical reaction chamber may be from 60 degrees to 120 degrees Fahrenheit. The pressure in the chemical reaction chamber may be from 1 atmosphere to 40 psig. The structurally altered gas molecule 240 has a hydrogen-oxygen-hydrogen bond angles between 94 degrees and 104 degrees and hydrogen-oxygen bond length between 0.95 Angstrom and 1.3 Angstrom. A hydrogen bonding of the structurally altered gas molecule 240 is neutralized. The structurally altered gas molecule 240, when being dissolved in water, may have two parts per million (ppm) of TDS, causing the TDS to reduce to one ppm. When being dissolved in the purified water, the structurally altered gas molecule 240 and the water may form a solution having a pH ranging from 6.1 to 6.8.

The structurally altered gas molecule 240 may be produced with a mixture of a hydroxide salt and an acid salt as the electrolyte. The structurally altered gas molecule 240 may have a density relative to a dry air of from 41.18% to 42%. The structurally altered gas molecule 240 may be stable at a pressure exceeding 300 psig. The structurally altered gas molecule 240 may have a peak at 600 inverse centimeters in an infrared spectrum.

In an example embodiment, upon dissolving the structurally altered gas molecule 240 in water, a solution of the structurally altered gas molecule 240 and water is produced. The solution may have an oxidation/reduction potential of −50 to −360 millivolts and pH from 6.1 to 6.8. The oxidation/reduction potential and the pH may remain stable for at least 30 days after the solution is placed in a closed insoluble vessel. When infused in water, the structurally altered gas molecule 240 may cause a hydrogen bonding in the water to be neutralized.

FIG. 3 shows a table 302 illustrating water analysis before and after treatment by the method of the present disclosure. The data in table 302 shows a 17.2% increase in salt rejection and a 16.7% decrease in TDS through the same RO membrane. It is important to note that a commercial grade RO membrane was used in this experiment (not a desalination membrane). The TDS measurements in table 302 for the RO feed and RO reject were made after a 50:1 dilution. As such, those numbers were averaged for consistency. Product TDS was measured neat 1:1 with no dilution. Product TDS numbers are well within the margin of error for the TDS measurement method used in this experiment. As expected, ORP measurements gave positive numbers with no treatment by the method of the present disclosure and negative numbers with the treatment by the method of the present disclosure. pH and temperature were found to be stable during all tests recorded in table 302 eliminating any related effects on the experiment.

FIG. 4 shows a table 402 illustrating transmembrane and osmotic pressure and flow data before and after treatment by the method of the present disclosure. Table 402 shows a 13.6% increase in RO product flow and a corresponding 13.6% decrease in RO reject flow. The transmembrane pressure was held at 199 psig during the entire experiment and yet minimum osmotic pressure to overcome the RO membrane in this experiment was decreased by 23.4% using the method of the present disclosure (94 psig before, 72 psig after treatment by the method of the present disclosure).

The data suggests that the energy gained from the observed decrease in osmotic pressure requirement may have increased product flow through the membrane. The fact that the salt rejection was increased, the TDS of the product was decreased, and the reject volume was decreased at the same time as the product flow was increased suggests that the method of the present disclosure is affecting the ion-ion, water-ion, water-water interactions in the manufactured brackish/seawater, and/or the membrane itself. Studies that involve charging RO membranes with electrons conclude that charging of the RO membrane has minimal effect on their performance. This suggests that the effect of the treatment by the method of the present disclosure is predominantly ion-ion, water-ion, and water-water related.

It is also important to note that a 23.4% pressure reduction corresponds to at least a linear reduction in energy use. This data in combination with the product flow increase and the reject flow decrease with no increase in feed flow to the RO membrane may conclude favorable economic and sustainability benefits.

FIG. 5 shows a table 502 illustrating economic and sustainability data using the method of the present disclosure on brackish/seawater RO membranes. Table 502 shows the 23.4% decrease in osmotic pressure number required to overcome the membrane and drive water through it. Using the global average of 16.47 kWh per 1000 Gallons (KGal), the observed RO product flow increase (increased water production with no increase in RO feed flow) and RO reject flow decrease (decreased waste water volume and cost) were used to create an economic and sustainability benefit summary shown in table 502. The analysis was documented in table 502 for both the average medium sized RO desalination plant and the average large sized RO desalination plant. Table 502 shows that the total annual water and energy savings are ~$5,000,000 USD for a medium sized RO desalination plant that prevents about 200 million Gallons of wastewater discharge per year. More than 10,000 MT of $CO_2$ is kept from being released each year to the atmosphere and over 700 persons are made carbon neutral from these energy savings.

For a large RO desalination plant, total annual water and energy savings are more than $15,000,000 USD, reducing about 780 million Gallons of wastewater discharge per year. More than 40,000 MT of $CO_2$ is kept from being released to the atmosphere each year and over 2800 persons are made carbon neutral from these energy savings.

The savings do not include the savings due to increased membrane life from reduced pressure exposure over time, or the possibility of reducing CAPEX for new builds that can now achieve more flow, 16.3% for the same construction costs. The $eCO_2$ benefits will provide considerable carbon offsets as well.

Conclusions. Passing manufactured brackish/seawater through a single stage, commercial, thin film composite RO membrane, pretreated with the method of the present disclosure yielded a 17.2% increase in salt rejection rate, 16.7% decrease in TDS in the product water, 13.6% increase in product water volume, 13.6% decrease in reject water volume and a 23.4% decrease in osmotic pressure required to initiate flow through the RO test membrane.

When using the method of the present disclosure as an RO pretreatment in the manufactured brackish/seawater, the results from this experiment show increased product water quality, increased product water flow volume, and decreased wastewater flow volume with less pressure (energy) requirement.

These results conclude a significant reduction in water and energy consumption, and increased sustainability benefit when using the method of the present disclosure in brackish/seawater RO desalinization applications.

When using the method of the present disclosure in existing medium RO desalination plants (30,000 $M^3$/day) and large RO desalination plants (120,000 $M^3$/day), (264.172 Gal/$M^3$), total annual water and energy savings are ~$5,000,000 USD for a medium sized RO desalination plant that prevents about 200 million Gallons of wastewater discharge per year. More than 10,000 MT of $CO_2$ is kept from being released each year to atmosphere and over 700 persons are made carbon neutral from these energy savings.

For a large RO desalination plant, total annual water and energy savings are more than $15,000,000 USD, reducing about 780 million Gallons of wastewater discharge per year to the environment. More than 40,000 MT of $CO_2$ is kept from being released to atmosphere each year and over 2800 persons are made carbon neutral from these energy savings.

The second experiment relates to effect of proprietary water restructuring on desalination of artificial seawater.

Summary of the second experiment. The process for restructuring water molecules of the present disclosure was tested for its ability to improve the efficiency of desalination of brackish water through reverse osmosis. Desalination was performed using up to 200 gallons of water per run at a driving pressure of 200 psi. Power consumption and product quality and flow were tested during 6 runs each using untreated and treated saline. Restructuring of the water molecules and their resulting interaction with the dissolved ions in solution prior to reverse osmosis desalination significantly altered the chemistry of the purified product, including lower TDS, with no decrease in product flow, no increase in reject flow, an increase in reject TDS, and no increase in power required to operate the reverse osmosis units.

Materials and methods. In the second experiment, bulk liquids were contained in high-density polyethylene tanks/totes that were cleaned with RO purified water prior to use. Saline was created by dissolving 125.45 kg of salts (instant ocean sea salt) into 10,600 liters of reverse osmosis purified water in a single 2800-gallon high-density polyethylene (HDPE) tank. The resulting solution had a TDS measurement of 10,750 mg/dl (1:1000 dilution, OHAUS ST200 TDS meter). Solution was maintained at room temperature and mixed each morning prior to use using a recirculating pump.

Figure 6:
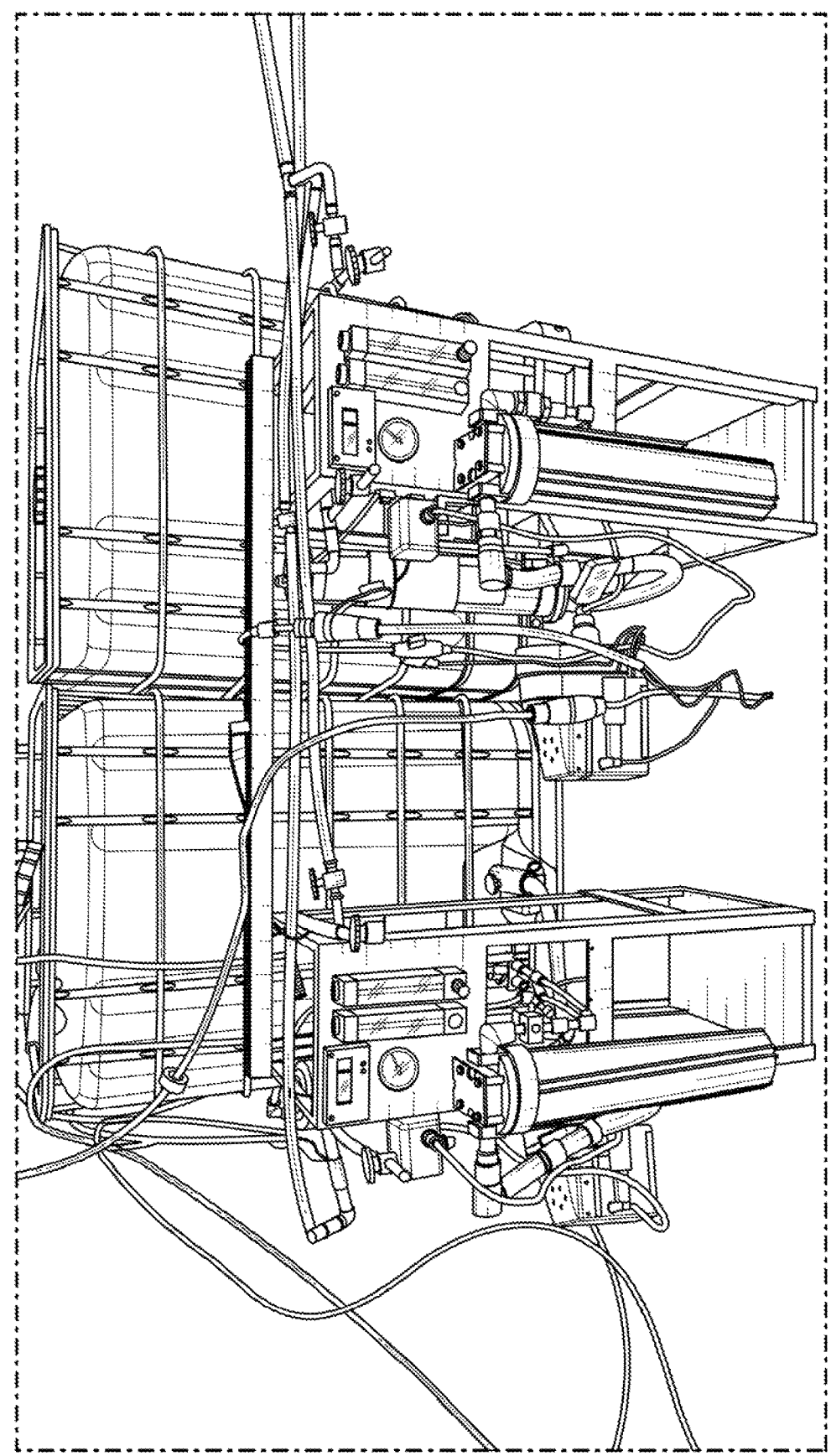
FIG. 6 shows duplicate RO systems used in an experiment according to the present disclosure.

FIG. 6 shows duplicate RO systems 602 that may be components of the system for enhancing water treatment and desalination and were used in the second experiment. The duplicate RO systems 602 are duplicate small-volume RO purification systems constructed to allow testing of untreated (control) and restructured saline. Each system consisted of a primary pump (Grundfos SCALA 2 Constant Pressure Pump) leading into a 2.5×20, 5 μm cartridge filter (Spiro Pure SP-P5-20) and then to a pressure-activated secondary pump (Dayton 484429A) which pumped the saline into an RO cartridge (BW 4021 UES, LG Chem). A digital flow meter (FMT3 Flow Meter, Tecalemit) was located inline between the primary pump and cartridge filter to record pump flow and totalized volume, and a pressure sensor (WIKA Type 0-300 psig FLW) was installed between the secondary pump and the RO cartridge to monitor head pressure. Product and waste flows from the RO cartridge were directed into float-style vertical flowmeters (Z-3001), with a metering valve installed on the waste flowmeter. Waste flow was then directed into an inline digital flowmeter (DM-P Series, Assured Automation) that reported both flow and totalized volume. Dual inline TDS meters (DM-2 Commercial In-Line Dual TDS Meter, HM Digital) were installed before (inlet line) and after (product line) the RO system cartridge. Product and waste flows exited the system through tubing that split into two streams: one stream exited the front of the system to allow for sampling of the flow, and the second stream exited the side for bulk discharge. Each of these streams was equipped with a ball valve to allow the flows to be directed as indicated by experimental protocol.

Figure 7:
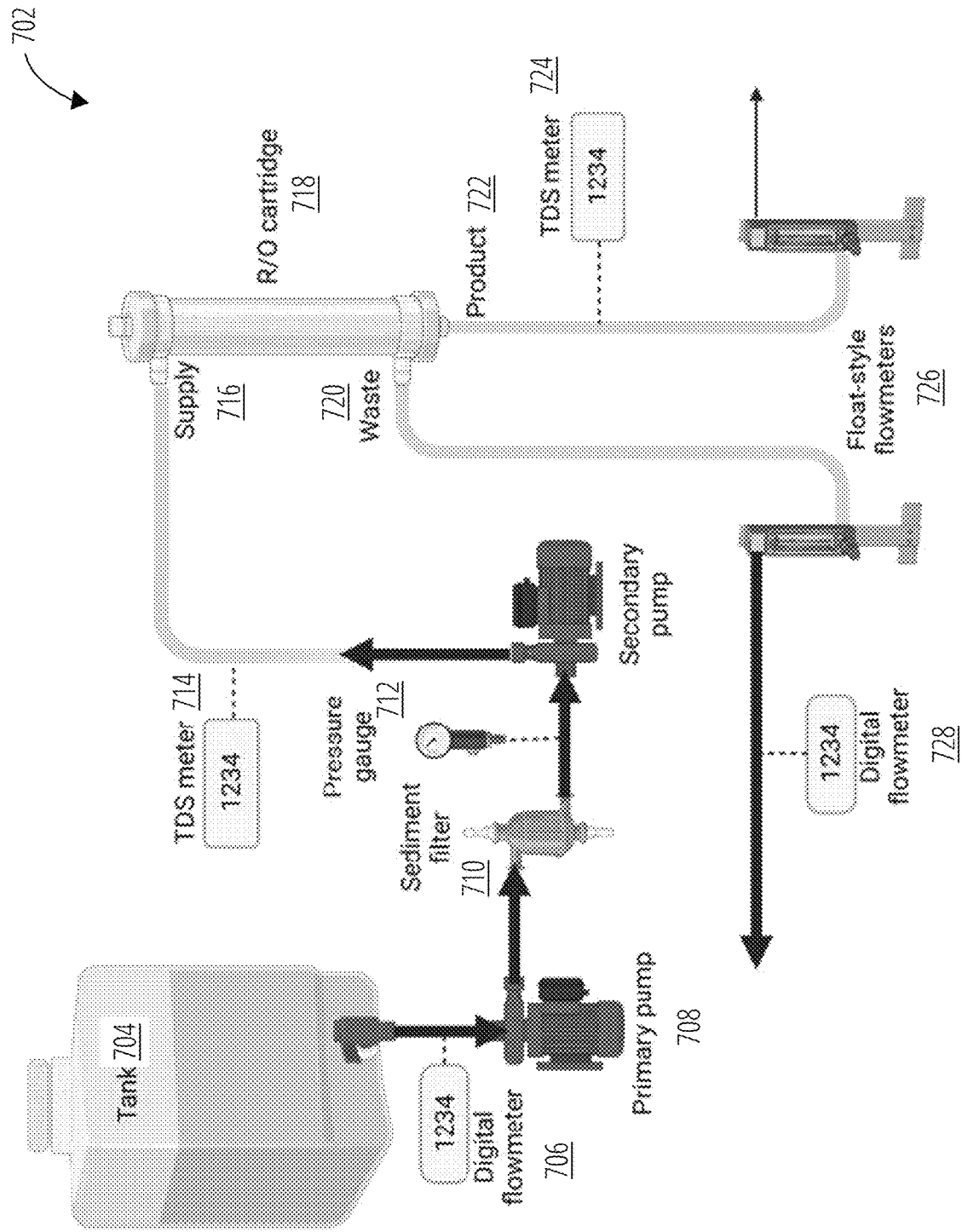
FIG. 7 shows a single RO system used in an experiment according to the present disclosure.

FIG. 7 shows a single RO system 702 that may be components of the system for enhancing water treatment and desalination and was used in the second experiment. The RO system 702 may include a tank 704, a first digital flowmeter 706, a primary pump 708, a sediment filter 710, a pressure gauge 712, a first TDS meter 714, a supply 716, a water filtering system shown as an RO cartridge 718, waste 720, a product 722, a second TDS meter 724, flow-style flowmeters 726, and a second digital flowmeter 728. In an example embodiment, the tank 704 may be filled with water mixed in the mixing chamber 210 shown in FIG. 2.

Saline was pumped into 2 300-gallon HDPE water totes immediately prior to a test run, and the restructured saline was gassed with proprietary gas for a minimum of 20 min to achieve a stable restructured condition (as confirmed by measured ORP of −200 mV). A new RO cartridge was installed for each test run in each system, and the system was flushed with a minimum of 20 gallons of RO purified water prior to starting the test. Complete flushing was confirmed by visual confirmation of the absence of bubbles in the product and waste flowmeters and a TDS value of 2-4 mg/dl on the product line (the TDS of the water being used to flush the system).

Water was pumped from the respective tote starting at time 0 with primary pump set to maximum flow. Upon activation of the secondary pump, the waste flow was adjusted using the metering valve on the vertical waste flowmeter to gradually bring the head pressure to 200 psi within the first 5 minutes of the test run. Head pressure was monitored continuously throughout the test run and the waste flowmeter was adjusted to maintain 200 psi head pressure. Every 15 minutes, the following parameters were recorded:

System electrical power (measured an ammeter on the common cord powering both primary and secondary pumps for a single system)
Primary pump flow
Primary pump totalized volume
System pressure
Waste flow
Waste totalized volume
Product flow (measured as mass (CPWplus-35) collected during a 1-minute timed diversion of product into a pre-weighed collection beaker)
Product TDS (inline meter)
Collected product TDS (Milwaukee EC-59 PRO EC/TDS/Temp probe)
Collected product pH (Hanna HI98129 pH/conductivity/TDS probe)
Collected product ORP (Apera ORP60 probe).

In addition, waste TDS was measured at 60 minutes and 120 minutes using a 1:1000 dilution with RO-purified water containing less than 2 mg/dl TDS. Each test was concluded after 120 minutes of continuous operation of the system. The assignments of the duplicate systems between Control and Restructured testing were established using a semi-random, balanced approach to allow for correction of minor system biases in the testing.

Figure 8:
FIG. 8 shows a table with summary data on the effect of saline treatment according to the present disclosure.

FIG. 8 shows a table 802 with summary data on the effect of saline treatment using the method of the present disclosure. Measurements within a single run were averaged prior to statistical analysis. Data were analyzed using 2 statistical approaches. First, data were tested for simple effects of both gas treatment and machine using paired t-tests, with data paired by run iteration and $p<0.05$ considered statistically significant. The effect of machine was included in the analysis due to observations during data collection that, despite construction of machines using identical components, there appeared to be differences in the saline flow through the machines under apparently identical conditions. If the simple effect of machine was significant, then the data were normalized to the variable mean value for each machine and reanalyzed using a t-test. Data also were analyzed for combined effects of gas treatment and machine using a 2-way Analysis of Variance (ANOVA). Due to the relatively low statistical power for this analysis, $p<0.1$ was considered significant.

Figure 9:
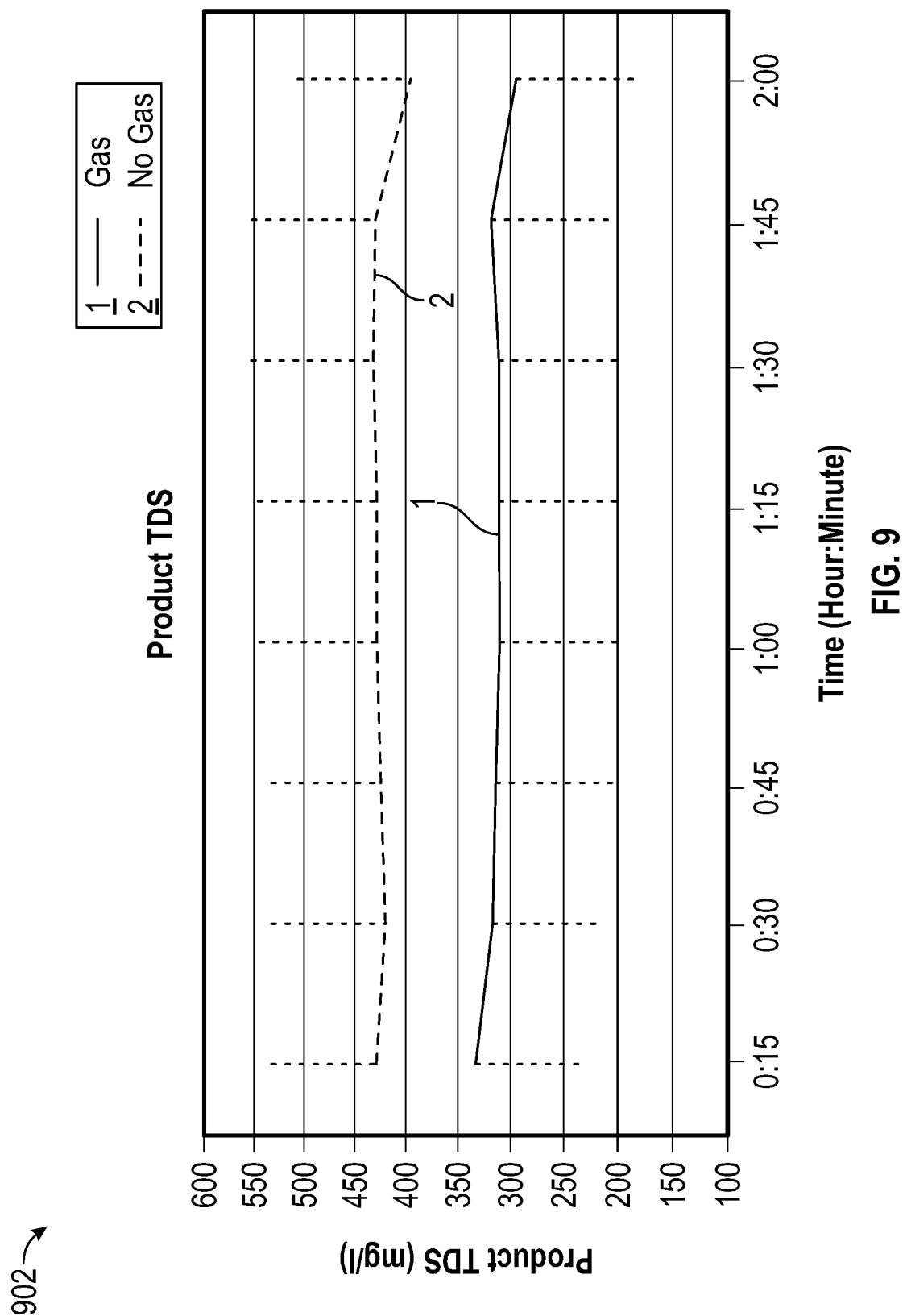
FIG. 9 is a diagram illustrating the effect of gas pretreatment on RO product total dissolved solids according to the present disclosure.

FIG. 9 is a diagram 902 illustrating the effect of gas pretreatment on RO product TDS. Data are the mean and standard deviation of 6 runs. There was a statistically significant effect of gas pretreatment on product chemistry when assessed by simple paired t-test, including TDS measured using the online meter ($p=0.04$) (FIG. 9), TDS measured using the handheld meter ($p=0.02$), ORP using both handheld meters ($p<0.001$), and pH ($p<0.001$).

Figure 10:
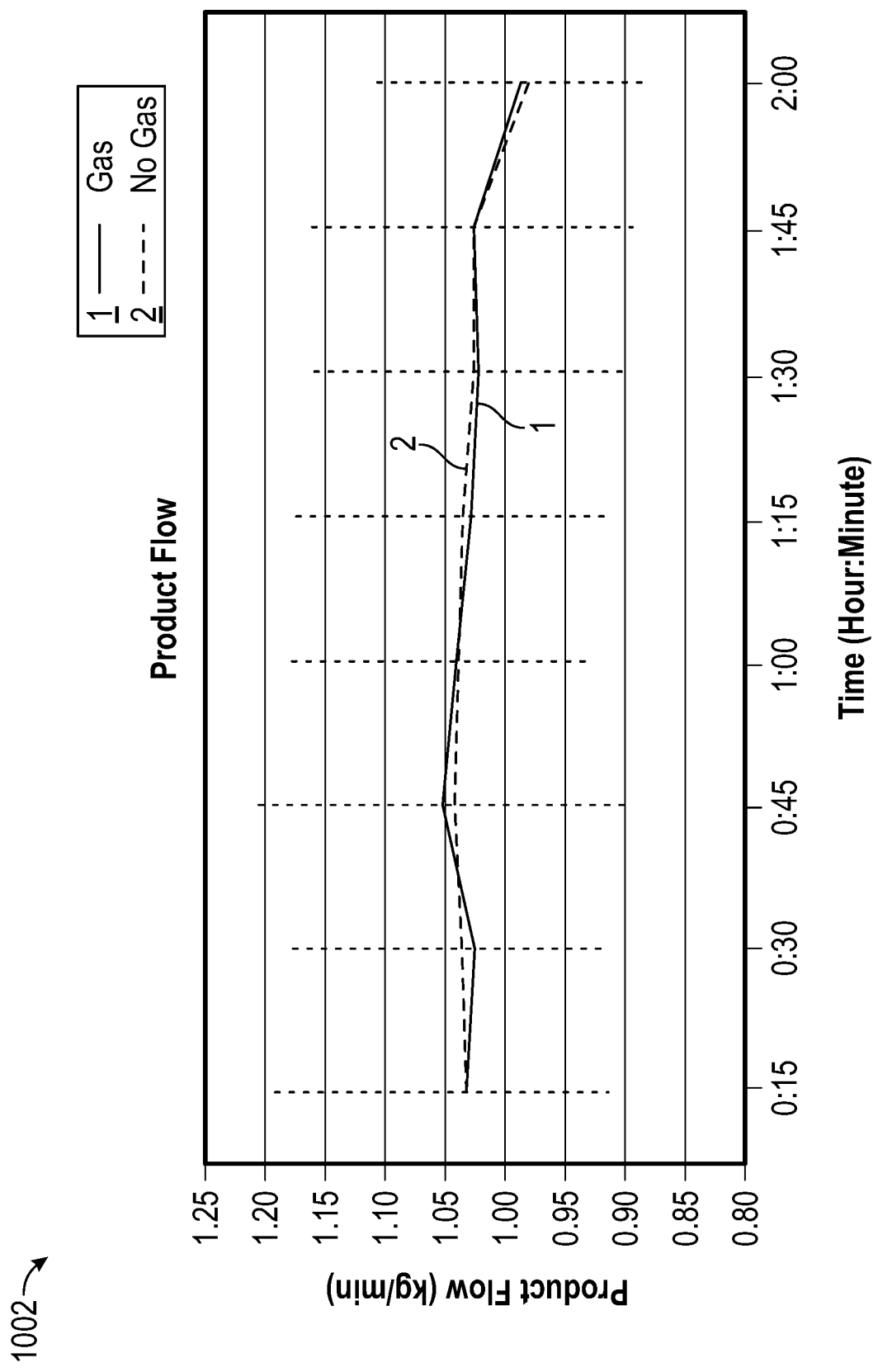
FIG. 10 is a diagram illustrating the effect of gas pretreatment on RO product flow rate according to the present disclosure.

FIG. 10 is a diagram 1002 illustrating the effect of gas pretreatment on RO product flow rate. Data are the mean and standard deviation of 6 runs. There was no effect of gas treatment on RO product flow ($p=0.49$). There was no statistically significant effect of gas pretreatment ($p=0.49$).

The experiment had a power of 0.80 to detect a difference of 0.24 kg/min of product flow or larger. Similar statistical results were obtained using 2-way ANOVA of the effects of both machine and gas treatment, although the effect of gas treatment on product TDS measured using the online meter failed to achieve statistical significance ($p=0.13$). There was no effect of gas treatment on the TDS of waste, although there was a trend ($p=0.09$) for the waste produced by gas-treated saline to have higher TDS than that of control saline. There was no effect of gas treatment on system electrical power ($p=0.16$), and there was a statistical power of 0.8 to detect a difference of 71.58 watts or larger. There was no effect of gas treatment on any other measured parameter.

There was a statistically significant effect of individual machines on system electrical power ($p=0.01$), primary pump flow ($p=0.007$), primary pump totalized volume ($p=0.02$), waste flow ($p=0.03$), and waste totalized volume ($p=0.004$). However, there was no effect of gas treatment when each machine's data for these variables was normalized to the mean of all six runs for that machine.

The data generated in this experiment indicate that pretreatment of saline with the method of the present disclosure results in altered chemistry of reverse osmosis product, including lower TDS, but does not affect the product flow rate or the power required to generate that flow.

Some of the chemistry changes are the direct result of this proprietary gas technology—specifically, the reduction in ORP and the increase in pH—as they are documented to be present prior to the reverse osmosis process. The reduction in TDS is secondary to that process and supports the conclusion that pretreatment facilitates increased removal of dissolved solids during the reverse osmosis process. The reduction in TDS with no decrease in product flow, no increase in reject flow and no increase in power required to operate the reverse osmosis units supports the hypothesis of reduction in intermolecular hydrogen bonding, a reduction in waters dipole moment and the resulting ion-dipole force that is formed between ions. These observations support the hypothesis that restructuring of artificial sea water immediately prior to RO purification decreases the TDS of the resulting RO product.

Figure 11:
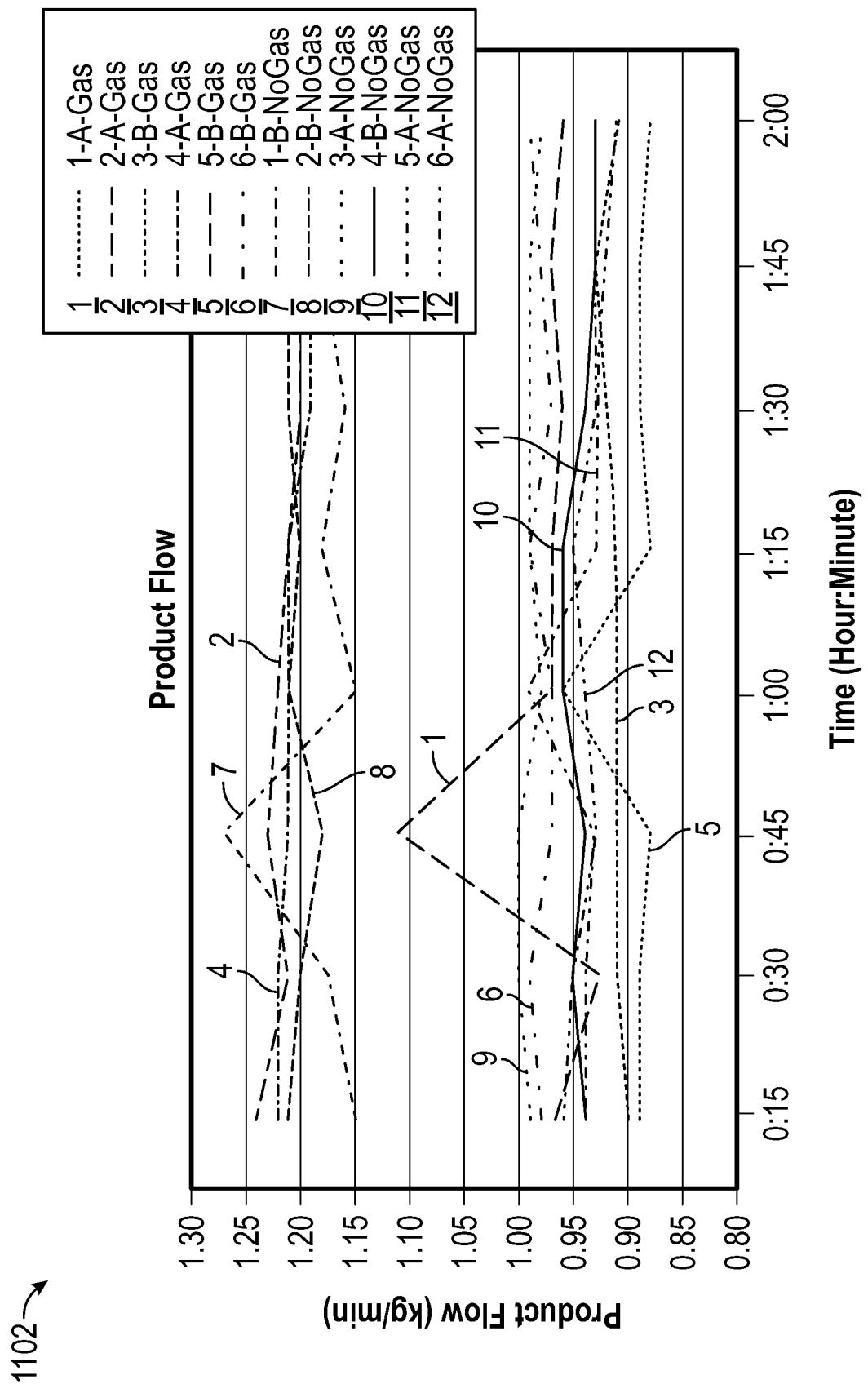
FIG. 11 is a diagram illustrating a product flow vs. time of individual reverse osmosis runs according to the present disclosure.

FIG. 11 is a diagram 1102 illustrating a product flow vs time of individual reverse osmosis runs. Each run is labeled with run number-machine ID-treatment (gassed or no gas control).

Figure 12:
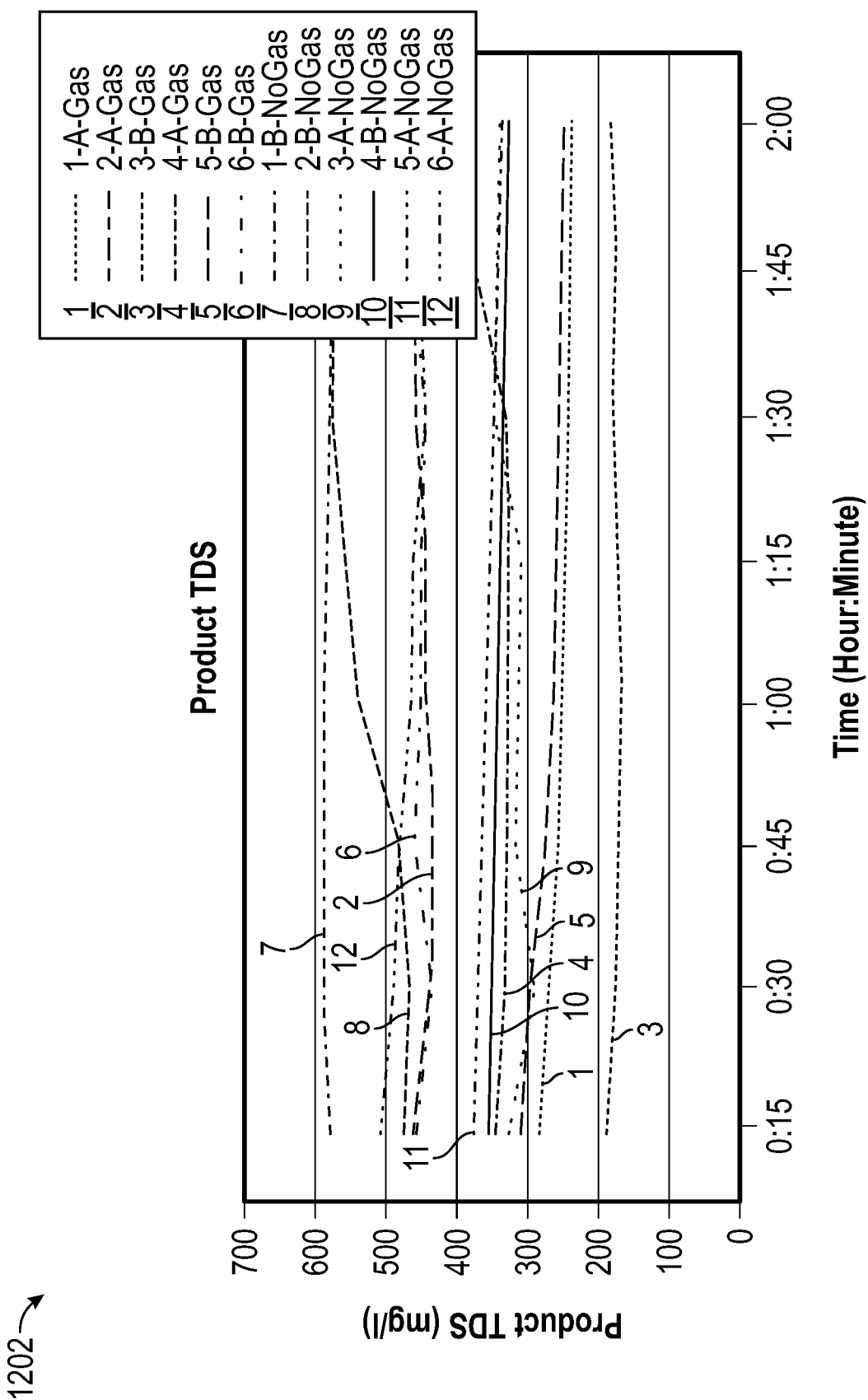
FIG. 12 is a diagram illustrating product total dissolved solids vs time of individual reverse osmosis runs according to the present disclosure.

FIG. 12 is a diagram 1202 illustrating product TDS vs time of individual reverse osmosis runs. Each run is labeled with run number-machine ID-treatment (gassed or no gas control).

A noteworthy finding in this experiment is the considerable variability in the performance of the RO cartridges in terms of both product flow rate (FIG. 11) and product TDS (FIG. 12). The cartridges are specifically labeled for the application in this experiment—purify brackish water—and were used within the manufacturer's specifications. The manufacturer states that the cartridges have an expected variability of ~15%, which is close to the variability measured in this experiment (12-14% coefficient of variation=standard deviation/mean×100%). However, this also means that an effect of gas pretreatment could be present but not be detected if that effect was smaller than the inherent variability in cartridge performance. An alternative approach would be to employ a cross-over experiment design in which the same cartridge was subjected to both treated and untreated saline in random order (with the appropriate washout between these steps) to eliminate cartridge variability as a factor in the experiment. Some measurement variability would remain (coefficient of variation of measurements within a single run was approximately 3-5%), but the statistical power of this approach would allow a detection of an effect as small as 3.5 kg/min if the cartridges performed consistently throughout the experiment (i.e., that the data obtained represented a steady state condition). In that regard, it is important to note that the current experiment design was based on the fact that the data in the pilot experiment suggested a lack of steady-state conditions during the first 2-3 hours of a run using a single new RO cartridge. Examination of the output of the individual runs in this experiment is inconclusive regarding a determination of steady-state conditions—in some cases, the data suggest changing performance within the 2 hour run and it is impossible to know how long the run would need to continue before a steady state was achieved.

Figure 13:
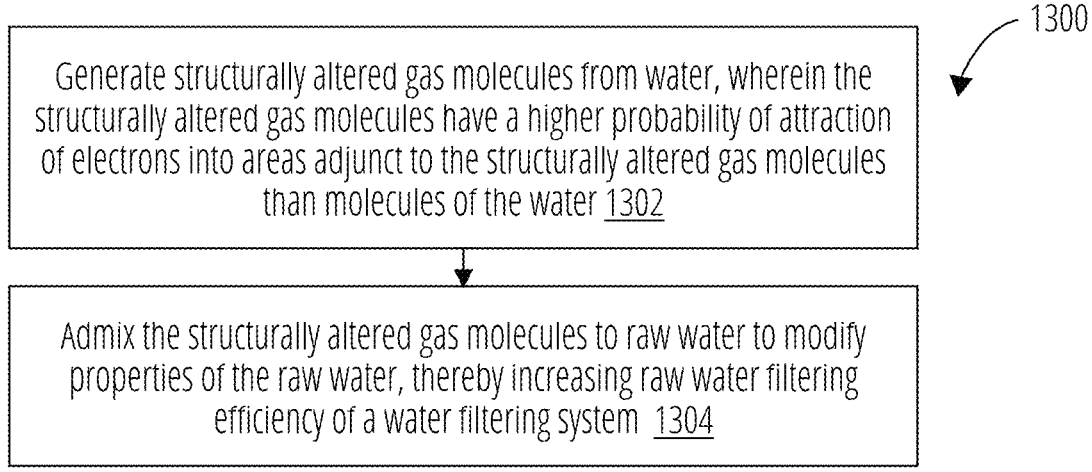
FIG. 13 illustrates a method for enhancing water treatment and desalination, in accordance with an example embodiment.

FIG. 13 is a flow chart of a method 1300 for enhancing water treatment and desalination, according to an example embodiment. In some embodiments, the operations may be combined, performed in parallel, or performed in a different order. The method 1300 may also include additional or fewer operations than those illustrated.

In block 1302, the method 1300 may commence with generating structurally altered gas molecules from water. The structurally altered gas molecules may have a higher probability of attraction of electrons into areas adjunct to the structurally altered gas molecules than molecules of the water.

In an example embodiment, the generation of structurally altered gas molecules may include placing an electrolyte solution in a chemical reaction chamber, adding purified water to the chemical reaction chamber, and applying a focused magnetic field and an electric field to a mixture of the purified water and the electrolyte solution to cause generation of the structurally altered gas molecule from the purified water. The structurally altered gas molecule may be a combination of two parts hydrogen and one part oxygen. The structurally altered gas molecule may have a hydrogen-oxygen-hydrogen bond angle between 94 degrees and 104 degrees and hydrogen-oxygen bond length between 0.95 Angstrom and 1.3 Angstrom.

The method 1300 may proceed in block 1304 with admixing the structurally altered gas molecules to raw water to modify properties of the raw water, thereby increasing raw water filtering efficiency of a water filtering system. In an example embodiment, the water filtering system may include a RO membrane.

In an example embodiment, the modification of the properties of the raw water may result in an increase of a product flow in the water filtering system by at least 13.6%. In some example embodiments, the modification of the properties of the raw water may result in an increase of a salt rejection in the water filtering system by at least 17.2%. In an example embodiment, the modification of the properties of the raw water may result in a decrease of a minimum osmotic pressure to overcome a reverse osmosis membrane by 23.4%. In some example embodiments, the modification of the properties of the raw water may include a decrease in pH from 7.0 to −6.5. In an example embodiment, the modification of the properties of the raw water may include a shift in a redox potential from 0 mV to ~−200 mV.

In an example embodiment, an oxidation/reduction potential of a solution of the structurally altered gas molecule and the purified water may be −50 to −360 millivolts. In some example embodiments, the oxidation/reduction potential may remain stable for at least 30 days after the solution is placed in a closed insoluble vessel.

Thus, systems and methods for enhancing water treatment and desalination have been described. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

What is claimed is:

1. A method for enhancing water treatment and desalination, the method comprising:
    generating structurally altered gaseous water molecules from water, the structurally altered gaseous water molecules having a chemical formula $H_2O$, wherein the structurally altered gaseous water molecules have a higher probability of attraction of electrons into areas adjunct to the structurally altered gaseous water molecules than molecules of the water;
    admixing the structurally altered gaseous water molecules to raw water to modify properties of the raw water and produce modified raw water; and
    treating and desalinating the modified raw water by passing the modified raw water through a water filtering system to produce a product water, the product water having a decreased amount of total dissolved salts as compared to the raw water passed through the water filtering system, thereby increasing raw water filtering efficiency of the water filtering system.

2. The method of claim 1, wherein the water filtering system includes a reverse osmosis membrane.

3. The method of claim 1, wherein the passing the modified raw water through the water filtering system includes producing a reject, the reject including substances filtered from the modified raw water.

4. The method of claim 1, wherein the passing the modified raw water through the water filtering system includes rejecting salts from the modified raw water by the water filtering system.

5. The method of claim 1, wherein the passing the modified raw water through the water filtering system includes providing a minimum osmotic pressure to overcome a reverse osmosis membrane.

6. The method of claim 1, wherein the generating the structurally altered gaseous water molecules includes decreasing pH from 7.0 to ~6.5.

7. The method of claim 1, wherein the generating the structurally altered gaseous water molecules includes shifting a redox potential from 0 mV to ~−200 mV.

8. The method of claim 1, wherein:
the generation of the structurally altered gaseous water molecules includes:
placing an electrolyte solution in a chemical reaction chamber;
adding purified water to the chemical reaction chamber; and
applying a focused magnetic field and an electric field to a mixture of the purified water and the electrolyte solution to cause generation of the structurally altered gaseous water molecules from the purified water, wherein:
a structurally altered gas molecule of the structurally altered gaseous water molecules is a combination of two parts hydrogen and one part oxygen; and
the structurally altered gaseous water molecules have a hydrogen-oxygen-hydrogen bond angle between 94 degrees and 104 degrees and hydrogen-oxygen bond length between 0.95 Angstrom and 1.3 Angstrom.

9. The method of claim 8, wherein the generating structurally altered gaseous water molecules includes providing an oxidation/reduction potential of a solution of the structurally altered gaseous water molecules and the purified water of −50 to −360 millivolts.

10. The method of claim 9, wherein the generating structurally altered gaseous water molecules includes maintaining the oxidation/reduction potential stable for at least 30 days after the solution is placed in a closed insoluble vessel.

11. A system for enhancing water treatment and desalination, the system comprising:
a chemical reaction chamber configured to accommodate water;
a magnetic field generator configured to generate a focused magnetic field;
an electric field generator configured to generate an electric field, wherein the electric field and the focused magnetic field drive a chemical reaction in the chemical reaction chamber to generate structurally altered gaseous water molecules from the water, the structurally altered gaseous water molecules having a chemical formula $H_2O$, wherein the structurally altered gaseous water molecules have a higher probability of attraction of electrons into areas adjunct to the structurally altered gaseous water molecules than molecules of the water;
a mixing chamber configured to admix the structurally altered gaseous water molecules to raw water to modify properties of the raw water and produce modified raw water; and
a water filtering system configured to treat and desalinate the modified raw water by passing the modified raw water through the water filtering system to produce a product water, the product water having a decreased amount of total dissolved salts as compared to the raw water passed through the water filtering system, thereby increasing raw water filtering efficiency of the water filtering system.

12. The system of claim 11, wherein the water filtering system includes a reverse osmosis membrane.

13. The system of claim 11, wherein the passing the modified raw water through the water filtering system includes producing a reject, the reject including substances filtered from the modified raw water.

14. The system of claim 11, wherein the passing the modified raw water through the water filtering system includes rejecting salts from the modified raw water by the water filtering system.

15. The system of claim 11, wherein the passing the modified raw water through the water filtering system includes providing a minimum osmotic pressure to overcome a reverse osmosis membrane.

16. The system of claim 11, wherein the generating the structurally altered gaseous water molecules includes decreasing pH from 7.0 to ~6.5.

17. The system of claim 11, wherein the generating the structurally altered gaseous water molecules includes shifting a redox potential from 0 mV to ~−200 mV.

18. The system of claim 11, wherein:
the generation of the structurally altered gaseous water molecules includes:
placing an electrolyte solution in the chemical reaction chamber;
adding purified water to the chemical reaction chamber; and
applying the focused magnetic field and the electric field to a mixture of the purified water and the electrolyte solution to cause generation structurally altered gaseous water molecules from the purified water, wherein:
a structurally altered gaseous water molecule of the structurally altered gaseous water molecules is a combination of two parts hydrogen and one part oxygen; and
the structurally altered gaseous water molecule has a hydrogen-oxygen-hydrogen bond angle between 94 degrees and 104 degrees and hydrogen-oxygen bond length between 0.95 Angstrom and 1.3 Angstrom.

19. The system of claim 18, wherein the generating structurally altered gaseous water molecules includes providing an oxidation/reduction potential of a solution of the structurally altered gaseous water molecules and the purified water of −50 to −360 millivolts.

20. The system of claim 19, wherein the generating structurally altered gaseous water molecules includes maintaining the oxidation/reduction potential stable for at least 30 days after the solution is placed in a closed insoluble vessel.

* * * * *